United States Patent [19]

Provost et al.

[11] 4,031,203

[45] June 21, 1977

[54] HEPATITIS A ANTIGEN

[75] Inventors: Philip J. Provost, Harleysville; Oswald L. Ittensohn, Telford; Maurice R. Hilleman, Lafayette Hill, all of Pa.

[73] Assignee: Merck & Co., Inc., Rahway, N.J.

[22] Filed: June 7, 1976

[21] Appl. No.: 693,668

Related U.S. Application Data

[62] Division of Ser. No. 530,623, Dec. 9, 1974.

[52] U.S. Cl. .................................................. 424/89
[51] Int. Cl.$^2$ ...................................... A61K 39/12
[58] Field of Search ...................................... 424/89

[56] References Cited

OTHER PUBLICATIONS

Feinstone et al. – Science vol. 182 Dec. 1973 pp. 1026–1028.

*Primary Examiner*—Sam Rosen
*Attorney, Agent, or Firm*—Donald J. Perrella; J. Jerome Behan

[57] ABSTRACT

Hepatitis A antigen obtained from the livers of non-human primates infected with hepatitis A (infectious hepatitis) virus has been found to be usable in fast, simple assays for hepatitis A antibody and thus usable in diagnosis of hepatitis A disease in humans, and for the preparation of hepatitis A vaccine.

3 Claims, No Drawings

HEPATITIS A ANTIGEN

This is a division of application Ser. No. 530,623, filed Dec. 9, 1974.

BACKGROUND OF THE INVENTION

This invention relates to hepatitis A (infectious hepatitis) antigen and to a method for its preparation, to its use in an assay for hepatitis A, and for the preparation of hepatitis A vaccine.

Hepatitis A is a liver disease which, while not commonly fatal, can involve many weeks of debilitating illness. It is usually spread by direct contact with an infected individual or by contaminated drinking water or food. Studies of hepatitis A have been hampered by the lack of a simple specific assay for antibody against hepatitis A virus. The development of such an assay has not heretofore been possible because no preparations have previously been available which contain hepatitis A antigen in such quantities as to enable the performance of complement fixation, immune adherence or other serologic assays. The only assays previously available were neutralization testing in marmosets (Provost et al., Proc. Soc. Exp. Biol. Med., 142, 1257, 1973) and immune electron microscopy (Feinstone et al., Science, 8 Nov. 1973) with fecal extracts. These methods were cumbersome, expensive and not applicable to routine testing.

It is, accordingly, an object of the present invention to provide a practical method for obtaining hepatitis A antigen. Another object is to provide hepatitis A antigen in sufficient quantities for use in an assay for hepatitis A. A further object is to provide a vaccine for hepatitis A. These and other objects of the present invention will be apparent from the following description.

SUMMARY OF THE INVENTION

Hepatitis A (infectious hepatitis) antigen is obtained from the liver of a non-human primate infected with hepatitis A virus. Extracts of the liver containing antigen both crude and purified, are usable in serological testing for hepatitis A antibody, and for the preparation of a vaccine for hepatitis A.

DETAILED DESCRIPTION

The hepatitis A (infectious hepatitis) antigen of the present invention is obtained from the liver of a non-human primate, e.g. a marmoset, such as a *Saguinus mystax* marmoset infected intravenously with hepatitis A virus. The liver of the primate is removed subsequently at a time when the serum glutamic oxaloacetic transaminase and serum isocitric dehydrogenase enzymes are elevated, which generally occurs at from about 14 to about 40 days after inoculation. The liver is perfused with physiological saline at a pH of from about 6.0 to about 7.8, for example, phosphate buffered saline solution containing 0,005M sodium phosphate and 0.143 M MaCl, pH 7.2. The liver is then disrupted to release subcellular constituents, e.g. by grinding, and mixed with physiological saline to give a final 10% suspension by weight. The antigen consists of the supernate obtained after clarification at low speed centrifugation, e.g. at from about 1,000 to about 2,000 rpm for a short period of time, e.g. for from about 5 minutes to about 15 minutes. The antigen in this form is applicable to performance of tests by complement fixation and immune adherence for hepatitis A antibody. The antigen in this form contains about $10^9$ of 27 m$\mu$ hepatitis A virus particles per cm$^3$.

The clarified supernate containing the antigen can be purified and fractionated by density gradient techniques, such as isopycnic and/or rate zonal methods. The density gradient separation, either isopycnic, or zonal, may be performed in media known to the art such as e.g., CsCl, NaBr, Na tartrate, sucrose and other materials of this type. The various fractions obtained from the separation are assayed against hepatitis A antibody for presence of hepatitis A antigen and gractions containing maximal hepatitis A antigen are selected. When carrying out the separation by buoyant density employing CsCl as the medium, hepatitis A antigen is recovered maximally from the fraction having a buoyant density of from about 1.32 to about 1.36 cm$^3$. The antigen in this form also contains about $10^9$ of 27 m$\mu$ hepatitis A virus particles per cm$^3$.

The antigen of the present invention is utilizable in an immunological assay for hepatitis A antibody. This assay is described in a copending application of William J. Miller and William McAleer, entitled "Immunoassay Method", filed concurrently herewith. The disclosure of that application is hereby incorporated by reference.

The hepatitis A antigen in any form whether derived from liver tissue or other tissues can be inactivated or attenuated for use as a vaccine against hepatitis A virus. Inactivation of infectivity may be achieved by treatment with formalin. The amount of formalin employed is effective to inactivate the infectivity of the antigen while retaining the immunogenicity such that the material is effective as a vaccine. Typically, formalin, 37% formaldehyde solution, is diluted in from about 1000 to about 10,000 parts of the antigen preparation and stirred at from about 4° C. to about 60° C. for about 2 hours to about 30 days, preferably the formalin is diluted in from about 2,000 to about 6,000 parts of the virus preparation at from about 20° C. to about 45° C. for from about 2 days to about 6 days, most preferably at about 37° C. for about 3 days.

The vaccine of the present invention may be used to immunize against hepatitis A virus in susceptible mamalian species such as, e.g. marmosets and chimpanzees.

The following examples illustrate the present invention without, however, limiting the same thereto.

EXAMPLE 1

Isolation of Antigen

Human hepatitis A virus is used to inoculate intravenously a *S. mystax* marmoset according to the procedure described by Mascoli et al. Proc. Soc. Exp. Biol. Med. 142, 276, (1973). The liver is removed 27 days after virus inoculation, at which time the serum glutamic oxaloacetic transaminase and serum isocitric dehydrogenase enzymes are elevated. The liver is perfused with phosphate buffered saline solution, pH 7.2 minced with scissors and ground in a mortar with sterile alundum and added to phosphate buffered saline to give a final 10% suspension by weight in the phosphate buffered saline. The antigen consists of 350 cc of supernate obtained after clarification by centrifugation at 1500 rpm for 10 minutes. The antigen at this stage contains greater than $10^9$ of 27 m$\mu$ hepatitis A virus particles per cm$^3$. The clarified antigen is then applied to a cesium chloride gradient tube covering the density range of from 1.1 to 1.4 g/cm³ and antigen having a buoyant density of from 1.32 g/cm³ to 1.36 g/cm³ is separated for use in the hepatitis A assay described in the previously mentioned copending application. This antigen contains about $10^9$ of 27 mµ hepatitis A virus particles per cm³.

EXAMPLE 2

Electron Microscopy of Infected Marmoset Liver

Small pieces of marmoset liver tissue, from animals infected with hepatitis A virus, are fixed in 1% osmium tetroxide, dehydrated in an ethanol series and embedded in Epon 812. Sections are cut on an LKB Ultramicrotome III using a diamond knife. Sections are picked up on copper grids, stained in uranyl acetate, post-stained with lead citrate and examined in the electron microscope. The virus closely resembles the enteroviruses in size and shape. The diameter is 27 mµ. The virus is present in the cytoplasm and tends to be localized in small vesicles that may be bound by multilayer membranes. The 27 mµ virus particles of the preparation are identified as hepatitis A virus by several criteria. Extracts of the liver are able to transmit hepatitis A infection to other marmosets. The virus is not present in normal marmoset livers. Identical 27 mµ virus particles are obtained from the blood of the infected marmoset. This preparation of 27 mµ virus particles is specifically neutralized by convalescent human hepatitis A serum but not by pre-illness serum.

EXAMPLE 3

Immune Electron Microscopy

Antigen, 0.05 ml., obtained as described in Example 1, is incubated with human convalescent hepatitis A sera, 0.02 ml. of a 1:20 dilution. The mixture is incubated at 37° C. for 1 hour and then held at 4° C. for a period of three hours. A drop of the material is placed onto a carbon-coated, 300-mesh copper grid, and allowed to adsorb for 30 seconds. The grid is then stained for 2 minutes with 2% aqueous phosphotungsic acid, pH 6.0 (adjusted with 1N KOH) and examined in a Phillips 300 electron microscope at 80KV. After reaction with hepatitis A antibody, characteristics halos of antibody molecules are seen to surround the numerous 27 mµ hepatitis A virus particles and to bind them into an immune complex.

EXAMPLE 4

Complement Fixation Assay

Antigen obtained as in Example 1 but prior to $C_sCl$ buoyant density gradient separation is heated for 2 hours at 56° C. This material is serially diluted and tested against serial dilutions of human hepatitis A antibody in standard block titrations by the microtiter method of complement fixation assay. Two units of antigen thus defined are used to subsequently assay human sera for hepatitis A antibodies. Hepatitis A antibody thus detected is specific to hepatitis A convalescent patients. The hepatitis B patients do not show hepatitis A antibody responses. This complement fixation assay using crude hepatitis A antigen from infected marmoset liver is usable in diagnosis of human hepatitis A infection.

EXAMPLE 5

The procedure of Example 1 is repeated employing in lieu of S. mystax individuals from the following genera and species: S. nigricollis, S. fuscicollis, S. oedipus, Callithrix jacchus, C. argentata, Cercopithecus aethiops, Pan troglodytes, and Anthropopithecus troglodytes. In each case the antigen obtained is successfully employed in the hepatitis A assay described in the previously mentioned copending application.

EXAMPLE 6

Both the clarified extract and the final product of Example 1 prepared under aseptic conditions are treated with 1:4000 formalin at 37° C. for 72 hours. Excess residual formalin is neutralized with sodium bisulfite. All treatments are performed under aseptic conditions. The product is stored at 4° C. Subcutaneous or intramuscular injection of 4 doses of 1 ml. given at 2 week intervals into S. mystax marmosets and quinea pigs induces circulating hepatitis A antibody in these animals. Further, the marmosets are rendered resistant to challenge with virulent doses of hepatitis A virus.

What is claimed is:

1. A method for obtaining hepatitis A antigen in an amount effective to complex hepatitis A antibody comprising inoculating a non-human primate with hepatitis A virus, subsequently removing the liver at a time when the serum glutamic oxaloacetic transaminase enzyme and the serum isocitric dehydrogenase enzyme levels are elevated, perfusing the liver with physiological saline, comminuting the liver and adding saline to obtain a suspension containing from about 5% to about 25% by weight of liver, clarifying the suspension, treating the suspension with CsCl gradient and selecting material having a buoyant density of from about 1.32 g/cm³ to about 1.36 g/cm³ of CsCl.

2. A method according to claim 1 wherein the non-human primate is a marmoset.

3. A method according to claim 2 wherein the marmoset is S. mystax.

* * * * *